(12) United States Patent
Erler (10) Patent No.: US 11,253,215 B2
(45) Date of Patent: Feb. 22, 2022

(54) METHOD FOR CORRECTING SCATTERED RADIATION IN A COMPUTED TOMOGRAPHY APPARATUS, AND COMPUTED TOMOGRAPHY APPARATUS

(71) Applicant: Carl Zeiss Industrielle Messtechnik GmbH, Oberkochen (DE)

(72) Inventor: Marco Erler, Oberkochen (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 0 days.

(21) Appl. No.: 16/926,373

(22) Filed: Jul. 10, 2020

(65) Prior Publication Data
US 2021/0007692 A1 Jan. 14, 2021

(30) Foreign Application Priority Data
Jul. 10, 2019 (DE) ...................... 10 2019 210 204.2

(51) Int. Cl.
*A61B 6/00* (2006.01)
*A61B 6/03* (2006.01)

(52) U.S. Cl.
CPC .............. *A61B 6/483* (2013.01); *A61B 6/032* (2013.01); *A61B 6/4291* (2013.01); *A61B 6/5282* (2013.01)

(58) Field of Classification Search
CPC ....... A61B 6/483; A61B 6/032; A61B 6/4291; A61B 6/5282
See application file for complete search history.

(56) References Cited

U.S. PATENT DOCUMENTS

| 4,466,113 A | 8/1984 | Strecker |
| 4,841,555 A | 6/1989 | Doi et al. |
| (Continued) | | |

FOREIGN PATENT DOCUMENTS

| DE | 24 52 166 A1 | 5/1976 |
| DE | 24 54 537 A1 | 5/1976 |
| (Continued) | | |

OTHER PUBLICATIONS

Schoerner, K., "Development of Methods for Scatter Artifact Correction in Industrial X-ray Cone-beam Computed Tomography", Dissertation, Physik Department, Technische Universitaet, Munich, Feb. 29, 2012, pp. i to 131.

(Continued)

*Primary Examiner* — Blake C Riddick
(74) *Attorney, Agent, or Firm* — Walter Ottesen, P.A.

(57) ABSTRACT

The invention is directed to a method for correcting scattered radiation in a computed tomography apparatus, wherein x-ray radiation emanating from an x-ray radiation source is divided into a plurality of partial beams by a grid structure such that irradiated regions and non-irradiated regions alternate, wherein a grid position of the grid structure is changed parallel to a detector surface. In a changed grid position, previously non-irradiated regions are irradiated and previously irradiated regions are not irradiated, wherein at least one radiograph of the test object is captured for each of the grid positions, wherein the radiographs captured at different grid positions are used to generate a bright field radiograph from the respectively irradiated regions and a dark field radiograph from the respectively non-irradiated regions and wherein a corrected radiograph is generated on the basis of the bright field radiograph and the dark field radiograph.

13 Claims, 5 Drawing Sheets

(56) References Cited

U.S. PATENT DOCUMENTS

| | | | |
|---|---|---|---|
| 6,408,049 B1* | 6/2002 | Edic | G01T 1/1648 |
| | | | 378/98.11 |
| 6,618,466 B1 | 9/2003 | Ning | |
| 7,352,840 B1* | 4/2008 | Nagarkar | A61B 6/032 |
| | | | 250/363.02 |
| 9,263,164 B2 | 2/2016 | Goldammer et al. | |
| 9,804,106 B2 | 10/2017 | Rothe | |
| 2002/0048339 A1* | 4/2002 | Schneider | G01T 1/1642 |
| | | | 378/7 |
| 2005/0220265 A1* | 10/2005 | Besson | A61B 6/4042 |
| | | | 378/16 |
| 2006/0067464 A1* | 3/2006 | Clinthorne | A61B 6/4233 |
| | | | 378/38 |
| 2008/0002807 A1* | 1/2008 | Debasish | A61B 6/00 |
| | | | 378/7 |
| 2008/0095313 A1* | 4/2008 | Ruhrnschopf | A61B 6/482 |
| | | | 378/98.4 |
| 2009/0020692 A1* | 1/2009 | Hoeschen | G06T 11/005 |
| | | | 250/252.1 |
| 2009/0135993 A1* | 5/2009 | Harer | A61B 6/585 |
| | | | 378/4 |
| 2009/0225938 A1* | 9/2009 | Zeitler | G01T 1/2985 |
| | | | 378/51 |
| 2014/0146935 A1 | 5/2014 | Goldammer et al. | |
| 2015/0243397 A1* | 8/2015 | Yun | A61B 6/4007 |
| | | | 378/36 |
| 2016/0258885 A1* | 9/2016 | Rothe | G01N 23/046 |
| 2020/0155098 A1* | 5/2020 | Jones | A61B 6/4241 |

FOREIGN PATENT DOCUMENTS

| | | | |
|---|---|---|---|
| DE | 25 48 531 | A1 | 1/1977 |
| DE | 38 26 288 | A1 | 4/1989 |
| DE | 90 17 465 | U1 | 4/1991 |
| DE | 91 03 670 | U1 | 5/1991 |
| DE | 100 51 728 | A1 | 5/2002 |
| DE | 10 2008 025 946 | B3 | 12/2009 |
| DE | 10 2010 020 150 | A1 | 11/2011 |
| DE | 10 2011 006 660 | A1 | 10/2012 |
| DE | 10 2011 087 806 | A1 | 6/2013 |
| DE | 10 2013 104 720 | A1 | 11/2013 |
| DE | 10 2015 102 334 | A1 | 9/2015 |
| EP | 0 057 957 | A1 | 8/1982 |
| EP | 0 230 155 | A1 | 7/1987 |
| EP | 1 476 077 | A2 | 11/2004 |
| JP | H05312733 | A | 11/1993 |

OTHER PUBLICATIONS

Zhu, L., et al, "Scatter Correction for X-ray Conebeam CT Using One-dimensional Primary Modulation", Medical Imaging 2009: Physics of Medical Imaging, edited by Samei, E. et al, Proc. of SPIE vol. 7258, 2009, pp. 725820-1 to 725820-8.

* cited by examiner

METHOD FOR CORRECTING SCATTERED RADIATION IN A COMPUTED TOMOGRAPHY APPARATUS, AND COMPUTED TOMOGRAPHY APPARATUS

CROSS REFERENCE TO RELATED APPLICATION

This application claims priority of German patent application no. 10 2019 210 204.2, filed Jul. 10, 2019, the entire content of which is incorporated herein by reference.

FIELD OF THE INVENTION

The invention relates to a method for correcting scattered radiation in a computed tomography apparatus, and to a computed tomography apparatus.

BACKGROUND OF THE INVENTION

X-ray radiation passes through a test object when measuring objects by means of computed tomography. Here, the x-ray radiation emanating from a focal spot of an x-ray radiation source is directed to an x-ray detector through the test object. The x-ray detector is used to capture, with a spatial resolution, an x-ray intensity of the x-ray radiation following a passage through the test object in the form of a radiograph. However, it is not only x-ray radiation striking a respective detector element of the x-ray detector after having passed along a straight line from the focal spot that is captured, but also scattered radiation which is generated in adjacent volume elements and which has traveled a different path to the detector element. This falsifies captured radiographs since the scattered radiation increases a signal background, a noise in a projection or in a radiograph and further generates unwanted artifacts in a reconstructed object volume. In particular, this can lead to deviations in an absolute material density in the reconstructed object volume. This represents a problem, particularly in the field of industrial computed tomography, where workpieces should be measured and checked precisely. Therefore, attempts are made to minimize or correct scattered radiation effects in captured radiographs.

U.S. Pat. No. 9,263,164 has disclosed a method and an apparatus for creating x-ray images of objects, in which artifacts caused as a consequence of scattered radiation are corrected. To this end, use is made of a modulator field which is movable from a first position into a second position. As a result of this, modulator field regions with a low x-ray radiation attenuation coefficient and with a comparatively high x-ray radiation attenuation coefficient in comparison therewith alternate. In each of the two positions, an original amplitude-modulated projection of the object is generated in each case and a stray image associated with the projection is calculated in each case.

DE 10 2011 087 806 A1 has disclosed a method and an apparatus for x-ray imaging with a conical x-ray beam, in which the x-ray beam is rasterized into a plurality of partial beams prior to the passage through the examination volume such that irradiated regions of the examination volume alternate with non-irradiated regions in a first recording geometry. Subsequently, one or more further recording geometries are set, in which the previously non-irradiated regions are irradiated and the previously irradiated regions are not irradiated at least in part. Then, the x-ray image is generated from the measurement values from the first recording geometry and from the one or more further recording geometries. Here, provision can be made for a scattered component of an irradiated region to be ascertained on the basis of a measurement of a region not irradiated at the same time.

The known methods only supply unsatisfactory results, particularly in the case of large gradients of the scattered radiation along a capture region of an x-ray detector.

SUMMARY OF THE INVENTION

An object of the invention is to develop a method for correcting scattered radiation in a computed tomography apparatus, and a computed tomography apparatus, by means of which scattered radiation can be corrected in improved fashion, particularly in view of locally strongly changing scattered radiation.

A method of the invention is for correcting scattered radiation in a computed tomography apparatus including an x-ray radiation source, an x-ray detector having a detector surface, a grid structure and a control device. The method includes the steps of: dividing x-ray radiation emanating from the x-ray source into a plurality of partial beams via the grid structure in advance of the emanated x-ray radiation passing through a test object so as to cause irradiated regions and non-irradiated regions of the test object to alternate; changing a grid position of the grid structure parallel to the detector surface in a direction of a grid period so as to cause, in a changed grid position, previously non-irradiated regions to be irradiated at least in part and previously irradiated regions to be non-irradiated at least in part with at least one radiograph of the test object being captured for each grid position; from the radiographs captured at corresponding ones of the grid positions, generating at least one bright-field radiograph from the irradiated regions and at least one dark-field radiograph from the non-irradiated regions; and, generating at least one corrected radiograph based on the generated at least one bright-field radiograph and the generated at least one dark-field radiograph.

The invention provides for x-ray radiation emanating from an x-ray radiation source to be split into a plurality of partial beams by means of a grid structure before the x-ray radiation passes through a test object and, as a result thereof, for irradiated and non-irradiated regions of the test object or irradiated and non-irradiated regions in a capture region of a detector surface of an x-ray detector to be developed. The irradiated and non-irradiated regions can be displaced by altering a grid position of the grid structure in the direction of a grid period parallel to the detector surface. This is implemented in such a way that, after the grid position has been changed, previously irradiated regions are non-irradiated at least in part and previously non-irradiated regions are irradiated at least in part. At least one radiograph is captured by means of the x-ray detector for each of the grid positions. In particular, provision can be made for a complete set of radiographs to be captured for each grid position in the case of a rotating object. In the complete set, a radiograph in each case corresponds to a specific rotary angle position of a rotary stage or of the test object. At least one bright field radiograph is generated from the respectively irradiated regions in the radiographs captured at different grid positions in each case. Accordingly, at least one dark field radiograph is generated from the respectively non-irradiated regions. Here, the bright field radiograph comprises both a signal of primary radiation of the x-ray radiation source, which has passed through the test object along a straight line, and a signal of scattered radiation or secondary radiation, which has arisen by scattering of the primary radiation.

Here, the signal of the scattered radiation or secondary radiation is reduced by the proportion covered by the grid structure. By contrast, the dark field radiograph only comprises a signal of the scattered radiation or secondary radiation which does not reach the respective detector element along a straight line, with the signal likewise being reduced by the proportion covered by the grid structure. Subsequently, at least one corrected radiograph is generated and provided on the basis of the generated at least one bright field radiograph and the generated at least one dark field radiograph. In particular, this is implemented by subtracting the dark field radiograph from the associated bright field radiograph. The at least one corrected radiograph is subsequently corrected for the scattered radiation. In particular, provision is made for all radiographs of the test object, which were captured at different rotary angle positions of the rotary stage or of the test object, to be corrected in this way. An object volume reconstructed from the corrected radiographs is consequently likewise corrected for the scattered radiation.

An advantage of the invention is that the scattered radiation can be captured and determined directly for all regions. The scattered radiation correction is therefore improved. A further advantage of the invention is that it is not necessary to capture a radiograph without a grid structure. All radiographs are captured with a grid structure disposed in the beam path. Therefore, a test object can be measured significantly faster since there is no need to provide or install and remove the grid. This leads to savings in terms of time and costs, particularly in the case of an application in in-line control in the production sector.

In particular, a method is provided for correcting scattered radiation in a computed tomography apparatus, wherein x-ray radiation emanating from an x-ray radiation source is divided into a plurality of partial beams by means of a grid structure before the x-ray radiation passes through a test object such that irradiated regions and non-irradiated regions of the test object alternate, wherein a grid position of the grid structure is changed parallel to a detector surface in the direction of a grid period such that, in a changed grid position, previously non-irradiated regions are irradiated at least in part and previously irradiated regions are not irradiated at least in part, wherein at least one radiograph of the test object is captured for each grid position, wherein the radiographs captured at different grid positions in each case are used to generate at least one bright field radiograph from the respectively irradiated regions and at least one dark field radiograph from the respectively non-irradiated regions and wherein at least one corrected radiograph is generated and provided on the basis of the generated at least one bright field radiograph and the generated at least one dark field radiograph.

Further, a computed tomography apparatus, in particular, is created, comprising an x-ray radiation source, an x-ray detector, a grid structure, and a control device, wherein the grid structure is disposed between the x-ray radiation source and the x-ray detector such that x-ray radiation emanating from the x-ray radiation source is divided into a plurality of partial beams by means of the grid structure before the x-ray radiation passes through a test object such that irradiated regions and non-irradiated regions of the test object alternate, and wherein the control device is embodied to alter a grid position of the grid structure parallel to a detector surface in the direction of a grid period by driving such that, in a changed grid position, previously non-irradiated regions are irradiated at least in part and previously irradiated regions are not irradiated at least in part, and to use the radiographs captured at different grid positions in each case to generate at least one bright field radiograph from the irradiated regions and at least one dark field radiograph from the non-irradiated regions, and to generate and provide at least one corrected radiograph on the basis of the generated at least one bright field radiograph and the generated at least one dark field radiograph.

In particular, provision is made for at least the at least one bright field radiograph to cover an entire capture region of the x-ray detector such that a complete radiograph can be provided.

In particular, the computed tomography apparatus is a computed tomography apparatus from the field of industrial metrology, that is, the computed tomography apparatus is configured, in particular, to measure and test workpieces.

The grid structure has a one or two-dimensional arrangement of grid elements. Preferably, the grid structure has a one-dimensional arrangement of grid elements. In particular, individual grid elements of the grid structure can consist of tungsten. Tungsten is advantageous in that it strongly absorbs x-ray radiation, that is, it has a relatively high absorption coefficient. As a result of this, it is possible, in particular, to use a grid structure with the smallest possible grid period of the grid elements. Further advantages are a great stiffness and relatively low procurement costs. However, in principle, other suitable materials can also be used.

In particular, provision is made for the computed tomography apparatus to have a positioning apparatus, wherein the positioning apparatus is embodied so as to be able to dispose the grid structures in the grid positions in controlled fashion. By way of example, the control device controls the positioning device by the provision of control signals. Further, provision can be made for the positioning apparatus to further be embodied in such a way that the grid structure can be removed from a beam path of the computed tomography apparatus and can be disposed therein again. This allows the grid structure to be disposed in a park position when it is not required.

Parts of the control device can be embodied, either individually or together, as a combination of hardware and software, for example as program code that is executed on a microcontroller or microprocessor.

In one embodiment, provision is made for non-irradiated regions and irradiated regions to each be masked in part when capturing the radiographs. Here, masking means that the captured measurement values of all detector elements are not taken into account. On account of a finite extent of the focal spot, the grid structure is imaged out of focus onto the capture region of a detector surface of the x-ray detector. Therefore, a sharp separation between irradiated and non-irradiated region is not possible at transitions between irradiated and non-irradiated regions. Rather, there is a continuous transition between irradiated and non-irradiated region. In order nevertheless to be able to sharply separate the regions, the unsharpness is taken into account when masking and so only regions lying outside of the unsharp region are used. In particular, masking is not carried out physically but only logically, for example by virtue of captured measurement values of detector elements in the masked regions being discarded after readout and by virtue of only using the measurement values of the non-masked detector elements. Consequently, a bright field mask is defined for the irradiated regions and a dark field mask is defined for the non-irradiated regions. By way of example, provision can be made for only half of the detector elements located in an irradiated or non-irradiated region to be taken into account in each case.

Moreover, masking in the non-irradiated region can also reduce an unwanted consideration of the point spread function, which is detector-dependent, between captured image values of individual detector elements of the x-ray detector. As a rule, an x-ray photon generates a multiplicity of photons in a scintillator material of the x-ray detector. In the process, the photons are emitted in all spatial directions. Therefore, the emitted photons are registered by a plurality of adjacent detector elements. This blurs a spatial resolution. This blurring effect can be reduced, particularly in the dark field radiographs, if a dark field mask is chosen such that use is only made of image values of detector elements substantially within the non-irradiated region, that is, at a distance from an edge of an adjoining irradiated region. Therefore, the capture of scattered radiation is improved in respect of spatial resolution. As a consequence, a correction of the scattered radiation in the bright field radiographs is also improved.

In one embodiment, provision is made for the grid positions to be chosen such that all regions of a capture region of the x-ray detector have captured an irradiated region at least once and a non-irradiated region at least once. As a result of this, it is possible to provide measurement values for the dark field radiograph, in particular for an entire capture region of the x-ray detector. Therefore, it is possible to dispense with an interpolation of captured measurement values in order to provide values for the regions at which no measurement value was captured. This is advantageous, in particular, in that each detector element has available a measurement value for the non-irradiated case. Therefore, a resolution of a dark field image used for correction purposes is maximal. This is particularly advantageous if the scattered radiation has a significant gradient in relation to adjacent detector elements. Therefore, there can be an improved correction of the scattered radiation, especially in the case of a significant gradient.

Provision is made in a developing embodiment for radiographs to be respectively captured for at least three grid positions, particularly when using a 50:50 grid structure with a one-dimensional arrangement of grid elements, which define open and closed regions of the same size. The grid positions are chosen in such a way that all regions of a capture region of the x-ray detector capture an irradiated region at least once and capture a non-irradiated region at least once. Even though it is not possible to dispose the grid structure with absolute precision, to moreover produce the grid structure with absolute precision, to align an image of grid elements of the grid structure exactly onto a boundary between detector elements or a pixel boundary and to image the grid structure with maximum sharpness on the detector, complete bright field radiographs and complete dark field radiographs can be generated in this way despite these imprecisions. Since, for example, there always is an overlap of the irradiated and non-irradiated regions in the case of a ratio of 50:50, caused by the grid structure with a one-dimensional arrangement of the grid elements, within the scope of capture in the at least three grid positions in successive measurements, these imprecisions of the grid can be neglected since the regions can be sharply subdivided on account of the overlap when using sharp boundaries between the detector elements or pixel boundaries. Naturally, in principle, more than three grid positions could also be provided.

If radiographs without a test object disposed in the beam path are captured for each of the at least three grid positions, it is possible to determine the masks for irradiated and non-irradiated regions in a simple manner. To this end, a search is carried out, for example, for maximum and minimum values or maximum and minimum regions in the radiographs captured without the test object, to find the respective grid positions. On the basis of the maximum and minimum values or regions determined, it is possible to exclude transition regions, caused by the above-described imprecisions, when setting the masks. Since radiographs are captured for at least three grid positions, an overlap between the irradiated and non-irradiated regions in the individual radiographs is so large in each case that masks with sharp boundaries with respect to one another can be defined for the three grid positions in each case and the above-described imprecisions following the masking of the captured radiographs can be neglected by using the masks defined in this way.

In one embodiment, provision is made for the corrected radiograph to be generated with at least one correction function being taken into account. This can prevent a value of a pixel of the corrected radiograph from lying below the dark noise of the detector on account of statistical noise in the dark field radiograph in combination with very low intensities in the bright field radiograph. On account of the Beer-Lambert law, this would lead to the assumption of great material thicknesses or material densities. This would lead to stripe artifacts in the reconstructed object volume because a very high material density affects all voxels under the respectively considered angle. In particular, the correction function ensures that large values of pixels in the dark field image are reduced such that, following the correction of the bright field radiograph by the dark field radiograph, there are no pixels with very low values of the order of the dark noise. Such a correction function can be used to reduce stripe artifacts in the reconstructed object volume.

In one embodiment, provision is made for radiographs without a test object to be captured for the grid positions before the radiographs of the test object are captured, the captured radiographs of the test object each being corrected on the basis of the associated radiographs captured without a test object. This allows effects caused by the grid and/or the x-ray detector to be removed from or corrected in the subsequently captured radiographs of the test object. In particular, this allows inhomogeneities and influences caused by the grid structure to be taken into account. By way of example, this is implemented by virtue of, in a first step, a number N1 of radiographs being captured with a deactivated x-ray source (dark images). The x-ray source is activated in a subsequent step and N2 radiographs (bright images) without a test object are captured at an x-ray power of 60-90% of an x-ray power subsequently used by measuring the test object (= reference intensity). An averaged dark image and an averaged bright image are created from the N1 captured dark images and the N2 captured bright images. This is implemented in each case for all envisaged grid positions. Pixels of captured radiographs (with a test object disposed in the beam path) can subsequently be corrected pixel-by-pixel as follows:

Radiograph_corrected=((Radiograph−Dark image)/
(Bright image−Dark image))*Reference intensity In one embodiment, provision is made for the grid structure to be chosen such that irradiated regions and non-irradiated regions are of equal size, at least in the direction of the grid period. This can simplify a procedure of the method since an increment when altering the grid position, for the purposes of covering an entire capture range of the x-ray detector, is the same size for both the irradiated regions and the non-irradiated regions.

In one embodiment, provision is made for the grid structure to comprise cylinder rods, the cylinder axes of which are disposed extending parallel to one another and perpendicular to an axis of rotation of a rotary stage of the computed tomography apparatus. In particular, a diameter of the cylinder rods ranges between one and a few millimeters. A perpendicular arrangement of the cylinder axis of the cylinder rods with respect to an axis of rotation is advantageous in that artifacts caused by the scattered radiation correction or by the grid structure are minimized. The cylinder rods disposed horizontally and parallel to one another form a one-dimensional grid structure, wherein associated edges of the grid structure are imaged horizontally on the x-ray detector. Possible changes in intensity at fixed locations and times in a correction result therefore lead to horizontal structures in each radiograph. Since pixels corresponding to an object volume element migrate horizontally from one side to the other during a movement in a stack of radiographs, which corresponds to a rotational movement of the test object about the axis of rotation, and since they possibly also migrate slightly in the perpendicular direction, there is averaging or compensating of artifacts possibly caused by the scattered radiation correction.

In an alternative embodiment, provision is made for the grid structure to comprise lamellas, which are in particular aligned on a focal spot with an inclination extending along a direction of a thickness of the lamellas, and which are disposed extending parallel to one another and perpendicular to an axis of rotation of a rotary stage of the computed tomography apparatus. In addition to the advantages of a perpendicular arrangement with respect to the axis of rotation of the rotary stage already described above, a use of lamellas is particularly advantageous if the work has to be carried out at high photon energies on account of object properties. The thickness of the lamellas can be adapted to the photon energy in the radiation direction for absorption purposes, without a width or height of the lamellas and/or a spacing of the lamellas from one another having to be adapted. By way of example, cylinder rods made of tungsten (see above) with a diameter of 2 mm are sufficient to achieve sufficient absorption of x-ray radiation at an acceleration voltage of 225 kVp. However, in order to achieve sufficient absorption even in the case of an acceleration voltage of 450 kVp, a diameter of 7-8 mm would be required, and so the grid structure with cylinder rods would have to have a very large grid period. In this case, lamellas would have better suitability as grid elements since a thickness in the radiation direction can be adapted independently of a height of the lamellas.

In one embodiment, provision is made for a position of the grid structure between the x-ray source and the x-ray detector to be chosen such that a magnification of the grid structure when imaging on the x-ray detector ranges between 1.8 and 3, preferably being around 2. This is based on the idea that the grid should be positioned as far away from the focal spot as possible in order to keep an unsharpness of the focal spot of the x-ray radiation source (also referred to as spot unsharpness) as small as possible. Here, the unsharpness of the focal spot is the greatest error influence when determining the irradiated and non-irradiated regions. Moreover, grid elements of the grid structure are also greatly enlarged in the case of a high magnification, and so this leads to large non-irradiated regions in an image representation on the x-ray detector. A negative influence of scattered radiation of the x-ray detector dominates at very high magnifications. This is due to the fact that only small test objects can be measured at high magnifications; these only supply little scattered radiation. Further, a test object is positioned at a great distance from the x-ray detector in the case of a large magnification; this leads to only a small portion of the scattered radiation striking the x-ray detector and the scattered radiation being largely homogeneous there and, as a result, acting like an offset. Since it is an object to determine the scattered radiation and secondary radiation occurring in a test object with a high spatial resolution, the magnification must therefore be chosen neither too large nor too small. Therefore, it was found to be advantageous to choose a magnification of the grid structure ranging between 1.8 and 3 when imaging onto the x-ray detector. This facilitates a magnification of a test object ranging between approximately 1.3 and 2. This can achieve a compromise between an imaged unsharpness of the focal spot, a size of the non-irradiated regions and a magnification of the test object such that the scattered radiation or secondary radiation occurring at the test object can be captured with an optimal spatial resolution.

In one embodiment, provision is made for the grid position to be changed while the test object rotates. This can reduce a measurement time when measuring a test object. A complete measurement run through for measuring a test object usually comprises a startup phase, in which a rotary table is driven into a start position and in which all moving parts are brought to an envisaged rotational velocity. This startup time is added to the measurement time, during which radiation is passed through the test object and radiographs are captured from different rotary positions. For reconstruction of the object volume, the test object has to be captured from all rotary positions for each grid position. After a complete revolution for a grid position, the grid structure must be brought into the next grid position; this requires a certain amount of time. In order to save further startup times after a first startup time, the test object or the rotary stage is rotated onward while the grid position is changed. While the grid structure is moved into a new grid position, the captured radiographs are discarded or no radiographs are captured during this time. This can be compensated by virtue of appropriately adapting a range of rotary positions in which the test object is captured. To this end, a rotary angle, after which captured radiographs are used or after which radiographs are captured, is adapted in successive iterations by the addition of a supplement, for example.

This is explained in the subsequent example, in which an assumption is made that a total of four grid positions are necessary to generate a complete bright field radiograph and a complete dark field radiograph. A first measurement iteration, in which the grid structure is disposed in a first grid position, is started at a rotary angle of −5°. In the case of a rotating test object or rotating rotary stage, radiographs in a suitable number are respectively captured at rotary angles of between 0° and 360°−n, where n denotes a rotary angle range that corresponds to a single radiograph (=360°/overall number of radiographs for one revolution). The grid structure is driven to the next grid position when a rotary angle of 360° is reached. An angular range, within which it is certain that the grid position has been fully changed, for example, 30°, is defined. However, the test object and the rotary table are rotated onward at a constant rotational angular velocity. In the second iteration, that is, with a grid structure disposed in a second grid position, radiographs are respectively captured at rotary angles between 1*360°+30° and 2*360°+30°−n. Subsequently, the grid structure is brought into the third grid position, with radiographs respectively being captured at rotary angles between 2*360°+60° and 3*360°+60°−n. For the fourth grid position, radiographs are respectively captured at rotary angles between 3*360°+90° and 4*360°+90°−n. A sequence of the captured radiographs or the associated rotary angles of the captured radiographs are subsequently resorted or corrected such that a complete revolution with the rotary angles between 0 and 360°−n can be provided for each grid position. Bright field and dark field masks used when generating the bright field radiographs and the dark field radiographs are defined according to this sequence.

Alternatively, a grid position can also be changed continuously; that is, the grid structure is moved continuously between a start position and an end position. In this case, a change in the grid position between two captured radiographs is negligibly small. However, it needs to be observed in the process that radiographs must be respectively captured for a specified minimum number of grid positions for each rotary angle of the rotary stage or test object. The specified minimum number is determined here by way of the number of grid positions at least required when taking account of defined masks so that a complete bright field radiograph and a complete dark field radiograph can be generated for each envisaged rotary angle. In this case, the masks are not stationary but change with the respective grid position. Therefore, it is important here that the grid position and the rotary angle are matched to one another.

Features relating to the configuration of the computed tomography apparatus arise from the description of configurations of the method. Here, the advantages of the computed tomography apparatus are respectively the same as in the configurations of the method.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
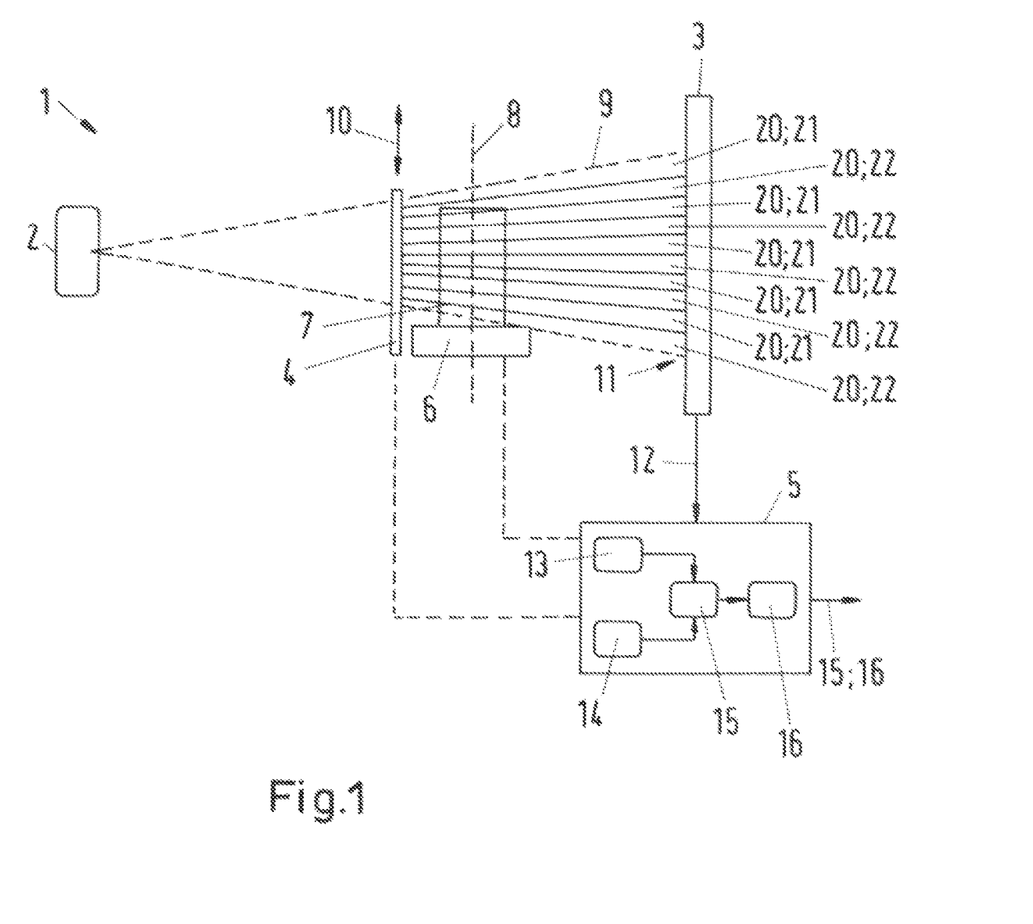
FIG. 1 shows a schematic illustration of one embodiment of the computed tomography apparatus.

FIG. 1 shows a side view of a schematic illustration of one embodiment of the computed tomography apparatus 1. The computed tomography apparatus 1 comprises an x-ray radiation source 2, an x-ray detector 3, a grid structure 4, and a control device 5. Further, the computed tomography apparatus 1 comprises a rotatable rotary stage 6, on which a test object 7 can be disposed and rotated about an axis of rotation 8.

The x-ray radiation source 2 generates conical x-ray radiation 9, which passes through the test object 7 and strikes a capture region of the x-ray detector 3.

Figure 2:
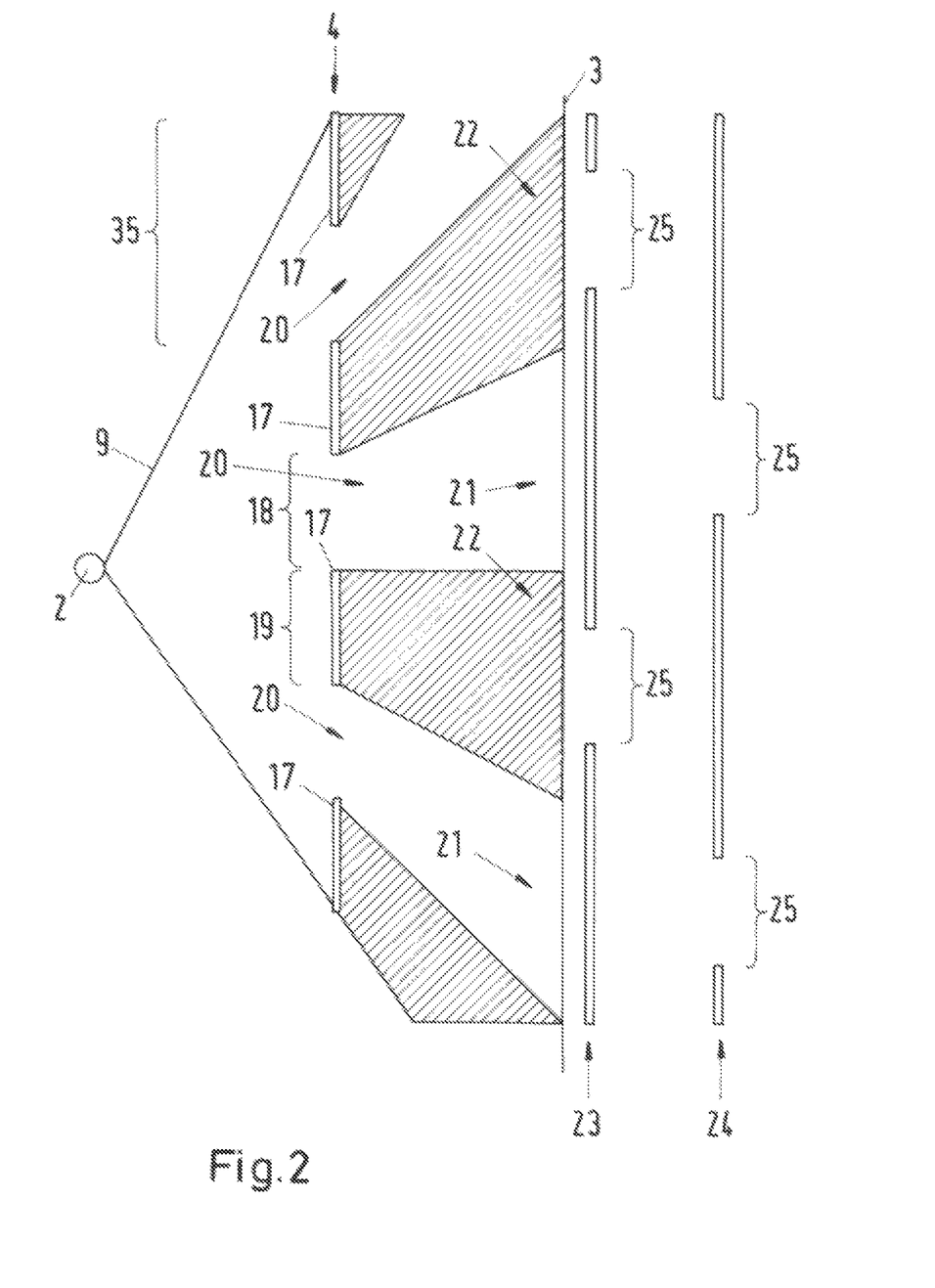
FIG. 2 shows a schematic illustration of an embodiment of the grid structure for elucidating the invention.

The grid structure 4 is disposed between the x-ray radiation source 2 and the x-ray detector 3 such that the x-ray radiation 9 emanating from the x-ray radiation source 2 is divided into a plurality of partial beams 20 by means of the grid structure 4 before the x-ray radiation passes through the test object 7, such that irradiated regions 21 and non-irradiated regions 22 of the test object 7, or on the x-ray detector 3, alternate (see also FIG. 2 for details).

In one embodiment, provision is made for the grid structure 4 to comprise cylinder rods, the cylinder axes of which are disposed extending parallel to one another and perpendicular to the axis of rotation 8 of the rotary stage 6 of the computed tomography apparatus 1.

Alternatively, provision can also be made for the grid structure 4 to comprise rectangular lamellas, which are disposed extending parallel to one another and perpendicular to the axis of rotation 8 of the rotary stage 6 of the computed tomography apparatus 1.

The control device 5 can change a grid position 10 of the grid structure 4 parallel to a detector surface 11 in the direction of a grid period by driving a linear drive (not shown), for example, such that, in a changed grid position 10, previously non-irradiated regions 22 are irradiated at least in part and previously irradiated regions 21 are not irradiated at least in part.

The control device 5 further controls a rotary position of the rotary stage 6.

From respective radiographs 12 captured at different grid positions 10, the control device 5 generates at least one bright field radiograph 13 from image values corresponding to the irradiated regions 21 and at least one dark field radiograph 14 from image values corresponding to the non-irradiated regions 22. On the basis of the generated at least one bright field radiograph 13 and the generated at least one dark field radiograph 14, the control device 5 generates at least one corrected radiograph 15 and provides the latter, for example by virtue of the at least one corrected radiograph 15 being output.

However, provision is made, in particular, for the control device 5 to collect the radiographs 15 that are captured for all grid positions 10 and all rotary angles of the rotary stage 6 and that are corrected according to the method and for the control device to reconstruct an object volume of the test object 7 therefrom and output the latter, for example in the form of object volume data 16.

FIG. 2 shows a schematic illustration of an embodiment of the grid structure 4 for elucidating the invention. Here, the grid structure 4 is represented by a simple shadow mask in simplified fashion. Here, the illustration is not true to scale and only serves for elucidating purposes. The grid structure 4 is disposed between an x-ray radiation source 2 and an x-ray detector 3, with a test object (not shown) being disposed between the grid structure 4 and the x-ray detector 3 when the test object is measured. The illustration shows a side view; individual grid elements 17 of the grid structure 4 extend parallel to one another for each grid period 35 and are disposed perpendicular (that is, extending perpendicular to the plane of the illustration of FIG. 2) in respect of an axis of rotation of a rotary stage of a computed tomography apparatus (cf. FIG. 1). A distance 18 between the grid elements 17 is exactly the same as a height 19 of the grid elements 17. The grid structure 4 is disposed between the x-ray source 2 and the x-ray detector 3 in such a way that a magnification of the grid structure 4 corresponds to a value of 2. In contrast to this simplified illustration, the grid structure 4 has a greater number of grid elements 17 in a real application of the method.

X-ray radiation 9 emanating from the x-ray radiation source 2 is divided into a plurality of partial beams 20 by means of the grid structure 4 such that irradiated regions 21 and non-irradiated regions 22 alternate. When a test object is disposed between the grid structure 4 and the x-ray detector 3, the partial beams 20 pass through the test object such that irradiated regions 21 and non-irradiated regions 22 also alternate in the test object.

Masks 23, 24 used for masking, which each partly mask the regions 21, 22, are schematically shown on the right-hand side of FIG. 2. Masking is carried out in order to take account of unsharpness effects, which arise on account of a finite extent of a focal spot of the x-ray source 2, by virtue of regions in the capture region of the x-ray detector 3, in which there is an edge unsharpness between irradiated regions 21 and non-irradiated regions 22, being discarded or not taken into account in the captured radiographs. There is a dark field mask 23 for the non-irradiated regions 22 and a bright field mask 24 for the irradiated regions 21. Here, the masks 23, 24 are only defined logically, that is, they have no physical correspondence but only serve to select pixels of the x-ray detector 3. Following a capture of a radiograph, only captured image values of pixels of the x-ray detector 3 that correspond to unmasked regions 25 are taken into account. By contrast, image values corresponding to other regions are discarded.

The masks 23, 24 shown in the example each mask ¾ of the overall area or of the test object, and so only ¼ of the pixels of a radiograph are used in each case. In order to be able to capture a test object in full, the grid structure 4 must therefore be disposed together with the masks 23, 24 in a total of four grid positions. This is implemented by virtue of the grid structure 4 being successively displaced into these four grid positions, for example, in the upward direction. A mask position of the masks 23, 24 is changed (logically) at the same time. After arranging the grid structure 4 in these four grid positions and capturing a respective radiograph in these four grid positions, the test object was completely captured or radiation has passed through the complete test object.

Figure 3:
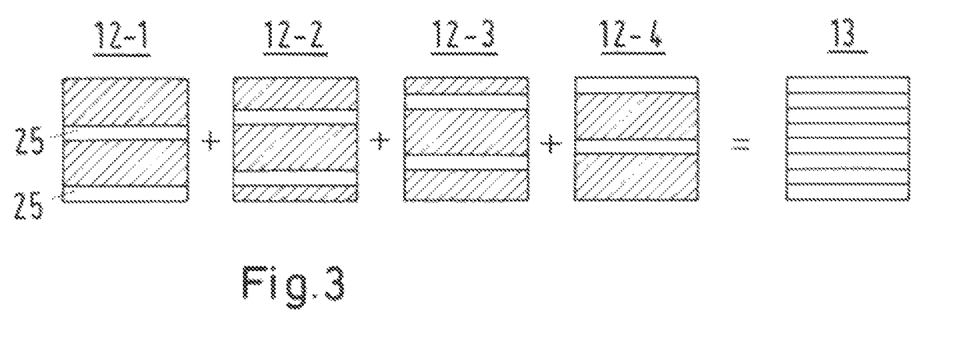
FIG. 3 shows a schematic illustration for elucidating the generation of a bright field radiograph or a dark field radiograph.

Subsequently, a bright field radiograph 13 is generated from the radiographs 12-$x$, which were respectively captured and masked for the four grid positions. The procedure is schematically illustrated in FIG. 3 for the grid structure 4 illustrated in FIG. 2 and the associated masks 23, 24. The generation is implemented by virtue of image values of pixels of the respectively non-masked regions 25 of the bright field mask 24 being combined with one another to form the bright field radiograph 13. Accordingly, a dark field radiograph 14 is generated by virtue of image values of pixels of the respectively non-masked regions 25 of the dark field mask 23 being composed to form the dark field radiograph 14 (in a manner analogous to FIG. 3).

Figure 4:
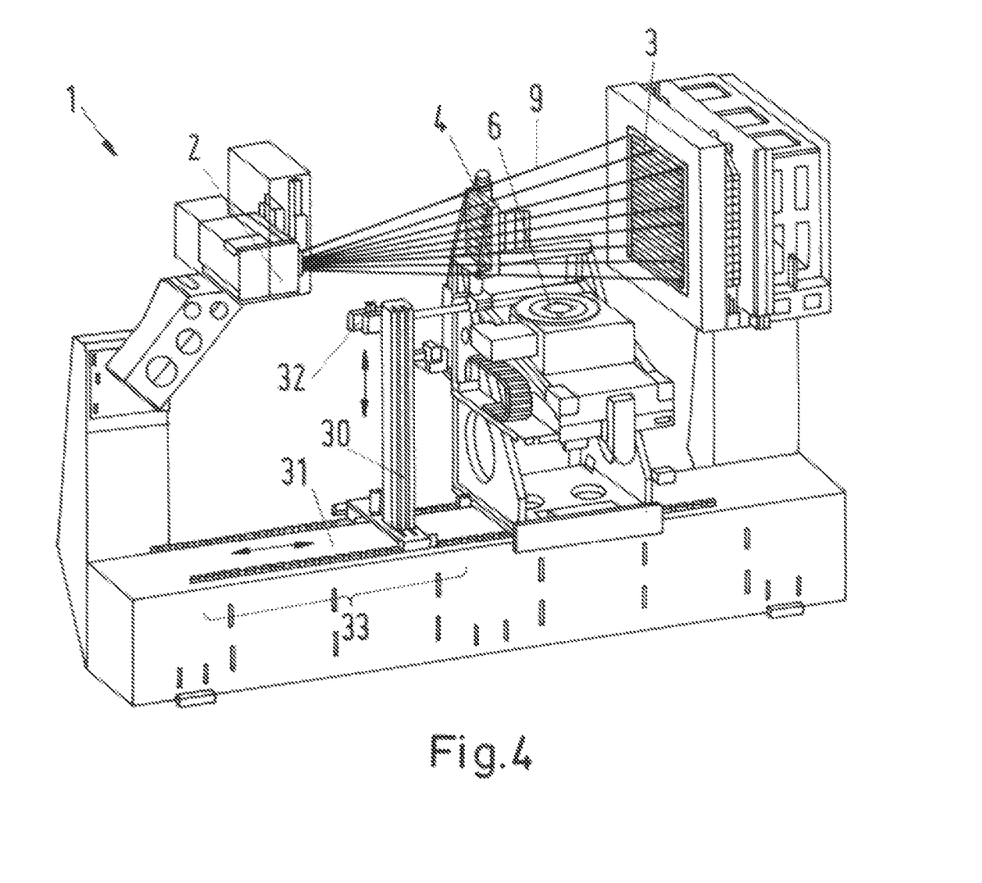
FIG. 4 shows a schematic illustration of a further embodiment of the computed tomography apparatus.

FIG. 4 shows a schematic illustration of a further embodiment of the computed tomography apparatus 1. Here, the shown embodiment substantially corresponds to the embodiment shown in FIG. 1; the same reference signs denote the same features and terms. For reasons of simplicity, the control device of the computed tomography apparatus 1 has not been shown.

The computed tomography apparatus 1 comprises a positioning device 33. The positioning device 33 comprises a grid holder 30, a rail 31, and a linear drive 32. By means of the grid holder 30, the grid structure 4 is disposed in a beam path of the computed tomography apparatus 1 and the grid structure can be displaced linearly along the beam path on the rail 31 such that a magnification of an image representation of the grid structure 4 on the x-ray detector 3 can be set. By way of the linear drive 32, the grid structure 4 can be brought into one of a plurality of grid positions in controlled fashion. Moreover, the grid structure 4 could be removed from the beam path by means of the grid holder 30 such that the grid structure 4 can be disposed in a park position (not shown) when not in use.

Figure 5:
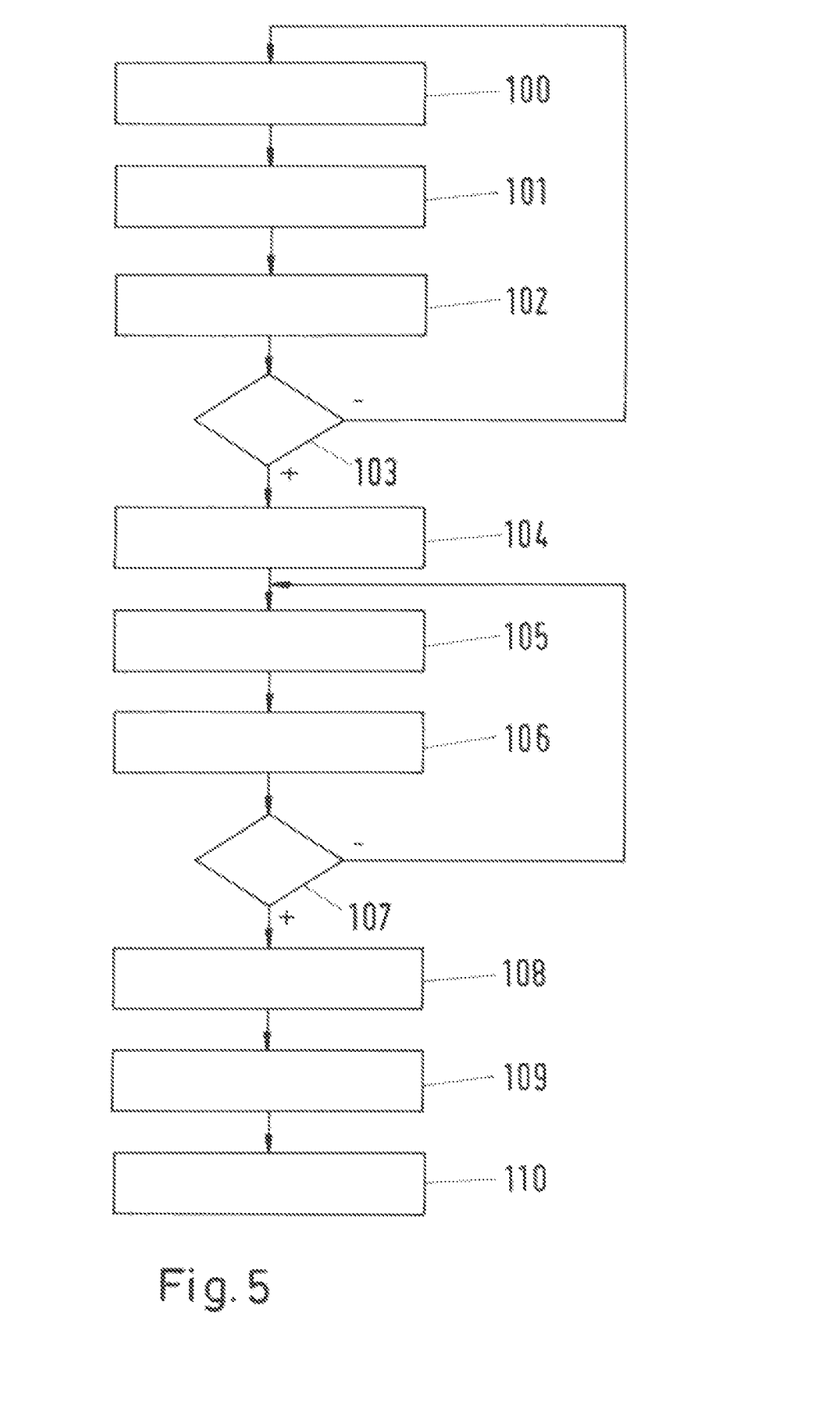
FIG. 5 shows a schematic flowchart of an embodiment of the method.

FIG. 5 shows a schematic flowchart of an embodiment of the method. In a method step 100, the grid structure disposed between x-ray source and x-ray detector is disposed in one of a plurality of grid positions. In the method step 101, a radiograph is captured with deactivated and activated x-ray source for each of these grid positions. The radiographs captured without a test object are taken into account later for correcting an influence of the grid.

In a method step 102, a bright field mask and a dark field mask for the associated grid position are generated from the radiograph captured with the activated x-ray radiation source. By way of example, this is implemented by virtue of regions of a captured x-ray intensity in the radiograph being subdivided into "bright", "gray" and "dark" regions. Depending on a number of grid positions, the bright field mask is defined from the "bright" regions and the dark field mask is defined from the "dark" regions. By contrast, interposed "gray" regions are masked by both masks, that is, image values in captured radiographs corresponding thereto are not used since the "gray" regions image an unsharpness of the focal spot.

In a method step 103, a check is carried out as to whether radiographs without a test object have already been captured for all envisaged grid positions. Should this not be the case, the method steps 100 to 102 are repeated for the remaining grid positions. For the purposes of altering the grid position, the grid structure is respectively displaced by a value $$dx=(\text{Grid period/Total number of grid positions})$$

parallel to a detector surface.

If radiographs are captured for all grid positions, a test object to be measured is disposed between the grid structure and the x-ray detector in a method step 104. This is implemented by disposing the test object on a rotary stage of the computed tomography apparatus.

In a method step 105, the grid structure is disposed in one of a plurality of grid positions, with all grid positions being taken into account again. Subsequently, at least one radiograph of the test object is captured in a method step 106. However, in particular, a complete set of radiographs is captured for all rotary angle positions of the rotary stage or of the test object. Within the scope of capture, the radiographs captured in method step 106 are each corrected with the aid of radiographs captured in method step 101 for the same grid position ("empty image correction").

In a method step 107, a check is carried out as to whether radiographs have already been captured for all envisaged grid positions. Should this not be the case, the method steps 105 and 106 are repeated. For the purposes of altering the grid position, the grid structure is shifted parallel to the detector surface by the value dx (see above) in each case.

Once radiographs have been captured for all grid positions, bright field radiographs and dark field radiographs are generated in a method step 108 from the captured radiographs on the basis of masks (cf. FIG. 2 and FIG. 3).

In a method step 109, the dark field radiographs are each subtracted from the associated bright field radiographs such that a corrected radiograph is generated in each case. The corrected radiographs are used in a method step 110 to reconstruct an object volume of the test object.

The method is advantageous in that scattered radiation can be captured directly and with spatial resolution for each region of a captured radiograph. As a result, a correction of the scattered radiation can be carried out in improved fashion.

In an alternative embodiment of the method, provision is made for the grid position to be changed while the test object rotates. This can reduce a measurement time when measuring a test object since it is possible to dispense with measurement pauses while the grid position is changed. This is taken into account accordingly when capturing the radiographs and when generating the bright field radiographs and the dark field radiographs.

In a further alternative embodiment of the method, a grid position can also be changed continuously. This is taken into account accordingly when capturing the radiographs and when generating the bright field radiographs and the dark field radiographs.

Figure 6A:
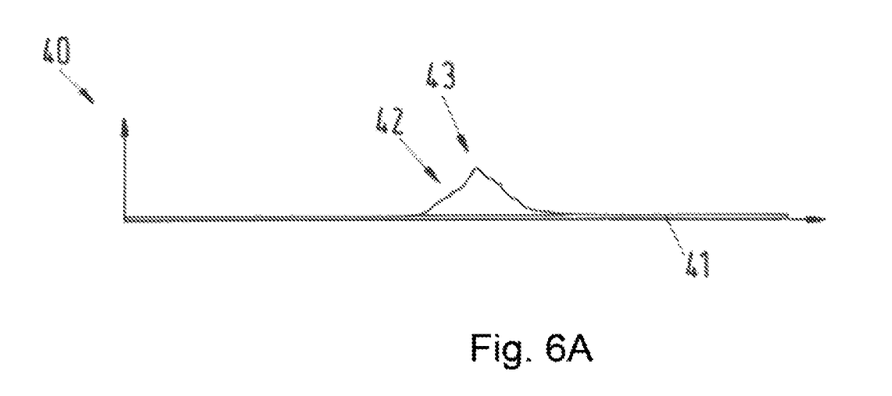
FIG. 6A shows a schematic illustration of a histogram of volume grayscale values in a reconstructed object volume (uncorrected); and, FIG. 6B shows a schematic illustration of a histogram of volume grayscale values in a reconstructed object volume (corrected).
Figure 6B:
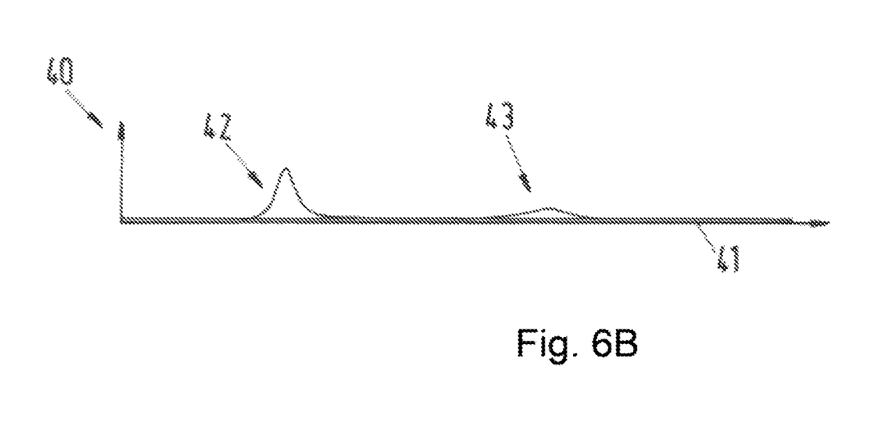

FIGS. 6A and 6B show schematic illustrations of histograms 40 of volume grayscale values 41 (x-axis) in reconstructed object volumes. In FIG. 6A, the reconstructed object volume was generated in this case on the basis of uncorrected radiographs. By contrast, in FIG. 6B, the reconstructed object volume was generated on the basis of radiographs that were corrected by means of the method.

In FIG. 6A, it is not possible to distinguish between background voxels 42 and test object voxels 43. By contrast, after the correction of the radiographs, the background voxels 42 can clearly be separated from the test object voxels 43.

It is understood that the foregoing description is that of the preferred embodiments of the invention and that various changes and modifications may be made thereto without departing from the spirit and scope of the invention as defined in the appended claims.

LIST OF REFERENCE SIGNS

1 Computed tomography apparatus
2 X-ray radiation source
3 X-ray detector
4 Grid structure
5 Control device
6 Rotary stage
7 Test object
8 Axis of rotation
9 X-ray radiation
10 Grid position
11 Detector surface
12, 12-x Radiograph
13 Bright field radiograph
14 Dark field radiograph
15 Corrected radiograph
16 Object volume data
17 Grid element
18 Distance
19 Height
20 Partial beam
21 Irradiated region
22 Non-irradiated region
23 Dark field mask
24 Bright field mask
25 Unmasked region
30 Grid holder
31 Rail
32 Linear drive
33 Positioning device
35 Grid period
40 Histogram
41 Volume grayscale values (x-axis)
42 Background voxel
43 Test object voxel
100-110 Method steps
100-109 Method steps

What is claimed is:

1. A method for correcting scattered radiation in a computed tomography apparatus including an x-ray radiation source, an x-ray detector having a detector surface, a grid and a controller, the method comprising the steps of:
   dividing x-ray radiation emanating from the x-ray source into a plurality of partial beams via the grid in advance of the emanated x-ray radiation passing through a test object so as to cause irradiated regions and non-irradiated regions of the test object to alternate;
   changing a grid position of the grid parallel to the detector surface in a direction of a grid period so as to cause, in a changed grid position, previously non-irradiated regions to be irradiated at least in part and previously irradiated regions to be non-irradiated at least in part with at least one radiograph of the test object being captured for each grid position;
   from the radiographs captured at corresponding ones of the grid positions, generating at least one bright-field radiograph from the irradiated regions and at least one dark-field radiograph from the non-irradiated regions; and,
   generating at least one corrected radiograph based on the generated at least one bright-field radiograph and the generated at least one dark-field radiograph.

2. The method of claim 1, wherein the non-irradiated regions and the irradiated regions are each masked in part when capturing the radiographs.

3. The method of claim 1, wherein the grid positions are selected such that all regions of a capture region of the x-ray detector have captured an irradiated region at least once and a non-irradiated region at least once.

4. The method of claim 3, wherein radiographs are respectively captured for at least three grid positions.

5. The method of claim 1, wherein radiographs without a test object are captured for the grid positions before the radiographs of the test object are captured, the captured radiographs of the test object each being corrected on the basis of the associated radiographs captured without a test object.

6. The method of claim 1, wherein the grid is selected such that the irradiated regions and the non-irradiated regions are of equal size, at least in the direction of the grid period.

7. The method of claim 1, wherein the grid comprises cylinder rods having cylinder axes disposed extending parallel to one another and perpendicular to an axis of rotation of a rotary stage of the computed tomography apparatus.

8. The method of claim 1, wherein the grid comprises lamellas which are disposed extending parallel to one another and perpendicular to an axis of rotation of a rotary stage of the computed tomography apparatus.

9. The method of claim 1, wherein a position of the grid between the x-ray radiation source and the x-ray detector is selected such that a magnification of the grid when imaging on the x-ray detector ranges between 1.8 and 3.

10. The method of claim 1, wherein a position of the grid between the x-ray radiation source and the x-ray detector is selected such that a magnification of the grid when imaging on the x-ray detector is 2.

11. The method of claim 1, wherein the grid position is altered while the test object rotates.

12. A computed tomography apparatus comprising:
an x-ray radiation source;
an x-ray detector having a detector surface;
a grid, and,
a controller,
said grid being disposed between said x-ray radiation source and said x-ray detector so as to cause x-ray radiation emanating from said x-ray radiation source to divide into a plurality of partial beams via said grid before said x-ray radiation passes through a test object causing irradiated regions and non-irradiated regions of the test object to alternate;
the controller being configured to change a grid position of said grid parallel to said detector surface in the direction of a grid period by driving said grid such that, in a changed grid position, previously non-irradiated regions are irradiated at least in part and previously irradiated regions are not irradiated at least in part; and,
said controller being configured to apply the respective radiographs captured at different grid positions to generate at least one bright field radiograph from the irradiated regions and at least one dark field radiograph from the non-irradiated regions and to generate and provide at least one corrected radiograph based on said at least one generated bright field radiograph and said at least one generated dark field radiograph.

13. A method for correcting scattered radiation in a computed tomography apparatus including an x-ray radiation source, an x-ray detector having a detector surface, a grid and a controller, the method comprising the steps of:
dividing x-ray radiation emanating from the x-ray source into a plurality of partial beams via the grid in advance of the emanated x-ray radiation passing through a test object so as to cause irradiated regions and non-irradiated regions of the test object to alternate;
changing a grid position of the grid parallel to the detector surface in a direction of a grid period so as to cause, in a changed grid position, previously non-irradiated regions to be irradiated at least in part and previously irradiated regions to be non-irradiated at least in part with at least one radiograph of the test object being captured for each grid position;
from the radiographs captured at corresponding ones of the grid positions, generating at least one bright-field radiograph from the irradiated regions and at least one dark-field radiograph from the non-irradiated regions;
generating at least one corrected radiograph based on the generated at least one bright-field radiograph and the generated at least one dark-field radiograph; and,
a position of the grid between the x-ray radiation source and the x-ray detector being selected such that a magnification of the grid is provided when imaging on the x-ray detector.

* * * * *